(12) United States Patent
Sak

(10) Patent No.: US 7,087,028 B2
(45) Date of Patent: Aug. 8, 2006

(54) METHOD AND APPARATUS FOR SAMPLING CERVICAL TISSUE

(75) Inventor: Robert F. Sak, Ft. Pierce, FL (US)

(73) Assignee: R&G Medical and Development Corp., Boca Raton, FL (US)

( * ) Notice: Subject to any disclaimer, the term of this patent is extended or adjusted under 35 U.S.C. 154(b) by 40 days.

(21) Appl. No.: 09/960,648

(22) Filed: Sep. 24, 2001

(65) Prior Publication Data
US 2002/0161313 A1    Oct. 31, 2002

Related U.S. Application Data

(63) Continuation-in-part of application No. 09/512,258, filed on Feb. 24, 2000, now Pat. No. 6,302,853.

(51) Int. Cl.
*A61B 10/00* (2006.01)

(52) U.S. Cl. .................................................... 600/569

(58) Field of Classification Search ........ 600/562–584; 606/160; 604/164.01
See application file for complete search history.

(56) References Cited

U.S. PATENT DOCUMENTS

| | | | |
|---|---|---|---|
| 1,867,624 A * | 7/1932 | Hoffman ..................... 600/567 |
| 2,767,703 A | 10/1956 | Nieburgs | |
| 2,955,591 A | 10/1960 | MacLean | |
| 3,774,590 A | 11/1973 | McDonald | |
| 3,776,219 A | 12/1973 | Brown | |
| 3,881,464 A | 5/1975 | Levene | |
| 3,995,618 A | 12/1976 | Kingsley et al. | |
| 4,059,404 A * | 11/1977 | Schuster et al. ............ 600/573 |
| 4,157,709 A | 6/1979 | Schuster et al. | |
| 4,175,008 A | 11/1979 | White | |
| 4,227,537 A | 10/1980 | Suciu et al. | |
| 4,396,022 A * | 8/1983 | Marx ......................... 600/571 |
| 4,586,604 A | 5/1986 | Alter | |
| 4,620,548 A * | 11/1986 | Hasselbrack ................ 600/571 |
| 4,628,941 A | 12/1986 | Kosasky | |
| 4,633,886 A | 1/1987 | Bucaro, Jr. | |
| 4,784,158 A | 11/1988 | Okimoto | |
| 4,788,985 A | 12/1988 | Manning et al. | |
| 4,803,998 A | 2/1989 | Kezes et al. | |
| 4,862,899 A | 9/1989 | Bucaro | |
| 4,877,037 A | 10/1989 | Ko et al. | |

(Continued)

OTHER PUBLICATIONS

"New Devices Aim at Improving Pap Test Accuracy", pp.1-5, Reprint of Oct. 1996 FDA Consumer.

(Continued)

*Primary Examiner*—Max F. Hindenburg
*Assistant Examiner*—Brian Szmal
(74) *Attorney, Agent, or Firm*—Banner & Witcoff, Ltd.

(57) ABSTRACT

A cervical sampling system for collecting a cervical sample for using a Pap test. The cervical sampling system includes an insertion tube with an insertion position indicator, and an introduction guide member that guides the insertion tube into a vaginal cavity. The vaginal insertion tube includes an insertion depth indicator to allow the user to determine the appropriate depth to insert the tube. A cervical sampler is positioned within the vaginal insertion tube and extends into the vaginal cavity to collect samples. The insertion tube and cervical sampler include signaling members that cooperate to indicate to the user when the cervical sample has been rotated through a complete revolution. After the cervical sample has been collected, an ethanol based fixative is applied onto the collecting member before it is forwarded to a lab for slide preparation.

22 Claims, 6 Drawing Sheets

U.S. PATENT DOCUMENTS

| | | | |
|---|---|---|---|
| 4,932,957 A * | 6/1990 | Zwick | 606/160 |
| 5,121,752 A | 6/1992 | Canna | |
| 5,251,641 A | 10/1993 | Xavier | |
| 5,370,128 A | 12/1994 | Wainwright | |
| 5,445,164 A | 8/1995 | Worthen et al. | |
| 5,449,071 A | 9/1995 | Levy | |
| 5,623,941 A | 4/1997 | Hedberg et al. | |
| 5,787,891 A | 8/1998 | Sak | |
| 5,795,309 A * | 8/1998 | Leet et al. | 600/569 |
| 5,836,451 A | 11/1998 | Dixon | |
| 6,155,990 A | 12/2000 | Fournier | |
| 6,206,839 B1 | 3/2001 | Zwelling-Aamot | |
| 6,302,853 B1 * | 10/2001 | Sak | 600/569 |

OTHER PUBLICATIONS

"The Wallach Papette Full Spectrum Cervical Cell Collector", Wallach Surgical Devices, Inc., pp. 1-2, 1999.

* cited by examiner

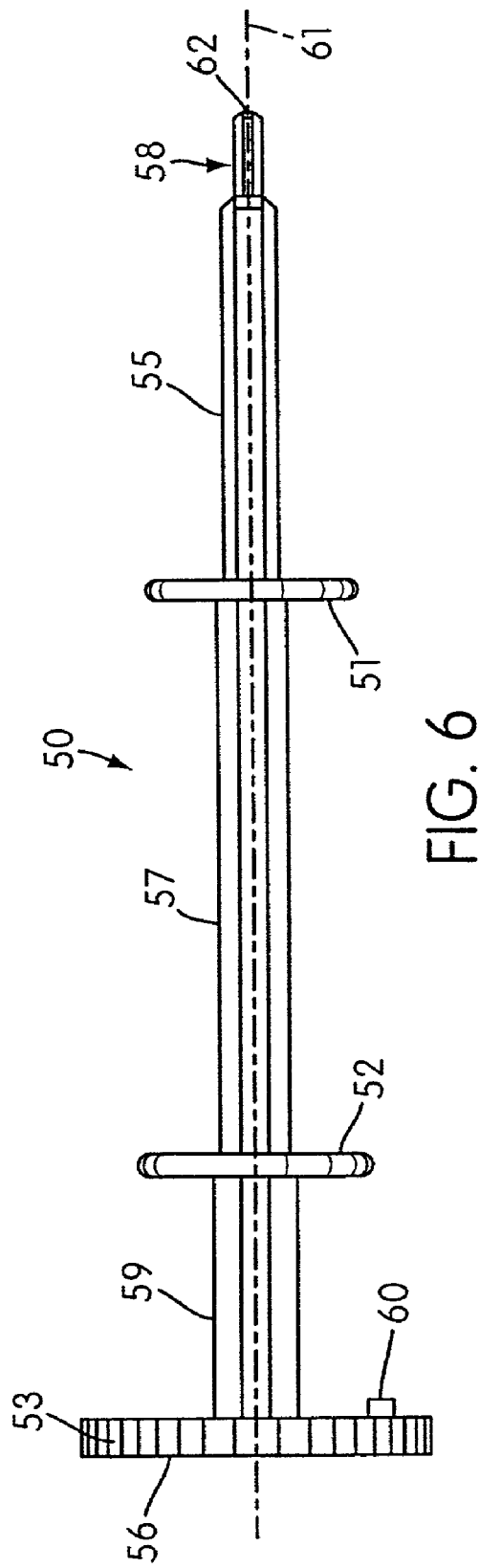
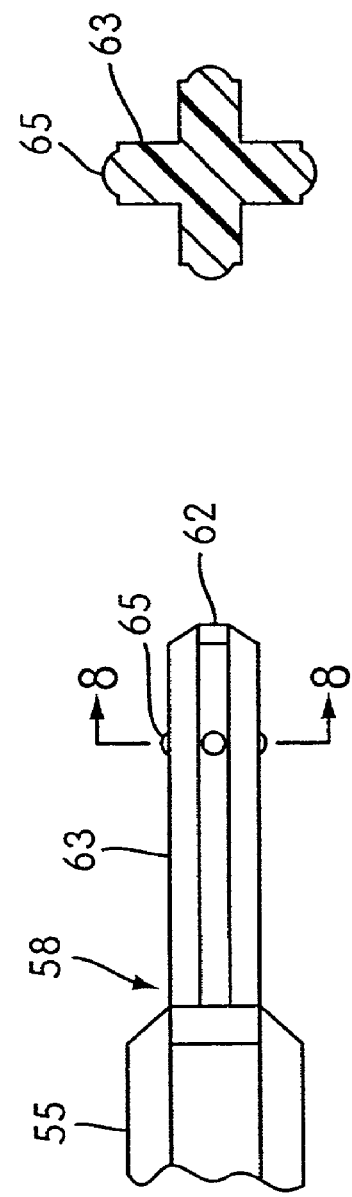

METHOD AND APPARATUS FOR SAMPLING CERVICAL TISSUE

This is a continuation-in-part of U.S. patent application Ser. No. 09/512,258 filed Feb. 24, 2000, now U.S. Pat. No. 6,302,853 which is expressly incorporated herein by reference. Benefit of the Feb. 24, 2000 filing date is claimed.

FIELD OF INVENTION

The present invention relates to an improved apparatus and system for obtaining a sample of cervical tissue and/or vaginal secretions such that pre-cancerous and cells may be detected. The present invention also relates to an improved method of using the sampling apparatus to collect samples and an improved method of preserving the collected cells for cytological examination.

BACKGROUND

Unlike many cancers that cause pain, noticeable lumps, or other early symptoms, cervical cancer has no telltale warning signs until it is so advanced that it is usually unresponsive to treatment. Only in the late stages does cervical cancer cause pain in the lower abdominal or back region, or produce other noticeable symptoms. Tests which provide early detection of cervical, uterine and vaginal cancer are paramount to the effective treatment and recovery from the disease. A Papanicolaou smear test, commonly referred to as a "Pap test", has long been established as a highly useful diagnostic tool that allows the identification of premalignant and malignant tissue at very early stages of the disease, as well as the identification of various inflammations and infections. The American Society of Clinical Pathologists recommends women have an annual Pap test.

A Pap test is a clinical procedure in which typically a bivalve speculum is inserted into a vaginal cavity and the cervix is exposed for sampling. A sample smear of cervical or vaginal secretions is then removed using an inserted scraper, probe, brush or similar type of device. The collected smear is evenly spread on one or more glass slides for microscopic examination. These standard-sized laboratory slides may be lined with hundreds of thousand of cervical cells. These slides are examined for the early detection of cancer or to determine the presence of certain hormonal conditions or certain infections. Lurking in these cells may be as few as a dozen abnormal cells. Finding such telltale cells is akin to finding a needle in a haystack, especially at the end of the day when laboratory technicians are likely to have examined countless Pap test slides. Therefore, the better the sampling and the better the cell preservation, the better the chance of detecting the presence of an abnormal cell. In addition, abnormalities in cell shape may be slight and difficult for even the trained eye to detect, or may be masked by infection.

At one time, Pap tests were performed almost exclusively by medical professionals in a doctor's office or a hospital. Many women, however, did not receive their yearly test because of their inability to visit a doctor on an annual basis, their reluctance to see a doctor or the expense of visiting a doctor coupled with test costs. As a result, self-administered, sample collecting kits or systems were developed so that women who did not go to the doctor on an annual basis could still be tested for abnormal cells. However, conventional self-administered sample collecting systems may not collect a sufficient amount of cervical tissue sample, or they may cause great discomfort to the user during use.

One such self-administered Pap test sampling collecting system is disclosed in U.S. Pat. No. 5,787,891 to Sak, that is herein incorporated by reference. This system includes a tubular speculum for inserting into the vaginal cavity, a guide sleeve located within the tubular speculum, and a swab assembly removably disposed within the guide sleeve. The swab assembly includes a sample collecting swab positioned within a swab sleeve in a retracted position when the device is first inserted into the vaginal cavity. A stem is then used for pushing the sample collecting swab out of the swab sleeve to an extended position and into contact with the cervical tissue. The sample collecting swab absorbs cervical samples until the user decides that enough sampling has been done.

Some patients may have difficulty using a self-administered sample collecting system because of the construction of its vaginal speculum. The speculum may be uncomfortable to insert into the vaginal cavity of the patient. The speculum may require the patient to use excessive force to push the speculum towards her cervix, thereby possibly causing an internal injury. Thus, the vaginal speculum may discourage women from taking the Pap test. Also, these self-administered sample collecting systems may not provide the user with the ability to determine the depth to which the vaginal speculum and the sampling device have been inserted into a vaginal cavity. The lack of proper insertion can lead to poor cervical samples and unreliable results.

Another problem that exists with conventional self-administered sample collecting systems for Pap tests is the inability of the patient to determine when enough of a sample has been obtained. Previous sampling systems do not effectively assist the patient in determining when the sampling device has been moved enough to obtain an adequate amount of sample. Improper sampling may give inaccurate test results, increase costs and discourage a woman from receiving testing at the recommended frequency.

A related problem exists with regard to the preparation and forwarding of a sample to a lab for analysis. As important as it is for the patient to collect a sufficient number of cells, it is also necessary that the maximum number of cells possible be sent to the lab. The more cells that can be properly preserved and transferred to the lab, the greater the chance that the lab can develop slides that will identify any cancerous or precancerous cells. Previous self-administered sample collecting systems have required the patient to place the collected sample on medical examination slides. This procedure can lead to an unsatisfactory specimen where bodily fluids can impede the diagnosis of the smear and prevent the atypical cells from being detected. This ineffective diagnosis can require the patient to repeat the procedure at a later time in order to obtain another sample.

To prevent patients from preparing slides and to provide labs with a large number of preserved cells from which to make slides, the sample collecting system disclosed in co-pending U.S. patent application Ser. No. 09/512,258 includes a sample collection container that carries a specific methanol-based thin layered preservative solution that is used as a transportation medium and in specimen preparation. This is at least in part because, as is known, conventional, ethanol alcohol-based cytofixatives typically used in slide preparation do not work effectively as transportation mediums and cell preservatives when provided in cell collection containers into which the sampling device is deposited for transporting to the lab. Therefore, the methanol-based preservative solutions have been used. Examples of the specifically developed solutions include CytoLyt® available from Cytyc® or a similar, specifically formulated thin layered preservative solution, such as Autocyte® PREP (or CytoRich®) available from Tri Path Imaging. However, these systems can be expensive to manufacture due to the high cost of the specific methanol-based thin layered preservative solutions that must be provided in the sample collection container. Additionally, the use of these special preservative solutions requires the lab that processes the sample to have expensive and state-of-the-art equipment. The cost of the sample systems and the state-of-the-art equipment needed to process and analyze the collected samples is so great that the use of these sample systems can be impractical in some parts of this country and certain poor sections of the world.

Thus, there is a need for an economical cervical sampling apparatus that can be effectively used by a woman performing sampling on herself. Further there is a need for an improved method of cervical sampling and an affordable, portable sampling system to advantageously provide for the detection of cancer.

It is an object of the present invention to overcome the aforementioned drawbacks in the conventional self-administered sample collecting systems for Pap tests.

An object of the present invention is to overcome the prior art problems of comfortably and effectively inserting a tubular speculum device in a vaginal cavity.

Another object of the present invention is to allow patients to readily determine when a sampling device has been rotated through a complete revolution so that the patient can keep an accurate count of how many times she has rotated the sample collecting device in order to achieve better sampling.

An additional object of the invention is to provide a sampling system that can provide useful, effectively preserved samples by using inexpensive, conventional ethanol alcohol-based fixatives.

SUMMARY OF THE INVENTION

In view of the foregoing, the present invention is directed to an improved system for collecting samples of cervical tissue and/or vaginal secretions. In addition, the present invention is directed to an improved method of using the sample collecting system for a Pap test. Moreover, the present invention relates to a method of applying a conventional, such as an ethanol based fixative, onto a cervical sampling device after a sample has been obtained.

The present invention includes a cervical sampling apparatus that has a vaginal insertion tube, an introduction guide member that is removably positioned inside the vaginal insertion tube and a cervical sampler that can be inserted within the vaginal insertion tube after the introduction guide member has been removed. The cervical sampler can be slid and rotated relative to the vaginal insertion tube when positioned therein. The cervical sampler includes a sample collecting member for obtaining a cervical sample.

The cervical sampling apparatus according to the present invention can also include the vaginal insertion tube having a signaling member and the cervical sampler including the sample collecting member, a handle, and an elongated body that extends along a longitudinal axis between the sample collecting member and the handle. The signaling member of the vaginal insertion tube cooperates with a signaling member of the cervical sampler to provide an audible or tactile signal to the user when the cervical sampler has been rotated past a reference point, thereby indicating that the cervical sampler has been rotated through a complete revolution.

In yet another aspect, the present invention includes an apparatus that can be positioned within a vaginal cavity. The apparatus includes a vaginal insertion tube and an introduction guide member for positioning within the vaginal insertion tube. The introduction guide member includes an elongated member and a guide head having a forward section that extends from the vaginal insertion tube when the introduction guide member is positioned within the tube. The forward section includes a substantially tapered conical area for introducing the vaginal insertion tube into the vaginal cavity. The guide head includes a passageway that extends through it and that is aligned with a passageway in the elongated member. These aligned passageways allow fluid within the vaginal cavity to pass through the introduction guide member in order to relieve pressure within the vaginal cavity.

Another aspect of the present invention comprises a method for cervical sampling. The method comprises the steps of introducing a cervical sampling member into a vaginal cavity, collecting a cervical sample from the vaginal cavity using the cervical sampling member and removing the cervical sampling member from the vaginal cavity. After the sampling member has been removed from the vaginal cavity, the method includes the step of applying an ethanol based fixative onto the cervical sampling member carrying the cervical sample.

The method according to the present invention can also include the steps of inserting the introduction guide member into the vaginal insertion tube so that a portion of the guide member extends outwardly from a forward end of the vaginal insertion tube, and introducing and advancing the vaginal insertion tube along with the inserted introduction guide member into a vaginal cavity. The introduction guide member is withdrawn from the vaginal insertion tube and the vaginal insertion tube is advanced further into the vaginal cavity until the vaginal insertion tube has reached a sampling position. Next, the cervical sampling member including a sample collecting member is inserted into the vaginal insertion tube. The sample collecting member is extended from the vaginal insertion tube so that the sample collecting member contacts a portion of cervical tissue. A cervical sample is collected with the sample collecting member.

According to the present invention, the invention has many advantages, including providing an introduction guide member that operates with a vaginal insertion tube or speculum to reduce the pain and discomfort a patient may experience while obtaining cervical samples. The present invention also provides an insertion depth indicator including a tactile portion on the vaginal insertion tube that allows a patient to reliably determine the appropriate depth of the tube in order to reduce discomfort during its insertion.

The cervical sampler according to the present invention allows for a reduction of the number of components and the number of steps needed to collect a sample as compared to conventional sampling systems. The cervical sampler and sample collecting member according to the present invention reduce manufacturing costs and allows a patient to readily perform a sampling procedure without having to manipulate numerous, separately moving parts.

The signaling members allow the patient to count the number of revolutions that the sample collecting member has undergone by either audibly or tactily indicating when a revolution has been completed. This feature improves the previous sampling procedures by ensuring that better and more complete cervical samples are collected.

By applying the conventional, ethanol based fixative onto the collected sample, the method of one embodiment of the present invention eliminates the need to provide an expensive, specially formulated methanol based preservative solution with the system. This reduces the overall cost of the sample collecting system and the cost of equipment needed at the lab that analyzes the samples collected with the present invention. For example, this embodiment of the method can eliminate the need for the specialized spinning or straining equipment used with the methods that have sample collection containers carrying methanol based preservative solutions, while simultaneously providing the lab with high cell concentrations for preparing effective slides.

These and other objects, features and advantages of the present invention will be apparent upon consideration of the following detailed description thereof, presented in connection with the following drawings in which like reference numerals identifying the elements throughout.

BRIEF DESCRIPTION OF THE DRAWINGS

FIG. 6 is a side view of the cervical sampler of FIG. 5 without the sample collecting member in accordance with the present invention;

FIG. 7 is a side view of a front end of the cervical sampler shown in FIG. 6;

FIG. 8 is a cross section of the front end shown in FIG. 7;

DETAILED DESCRIPTION OF THE PREFERRED EMBODIMENTS

Figure 1:
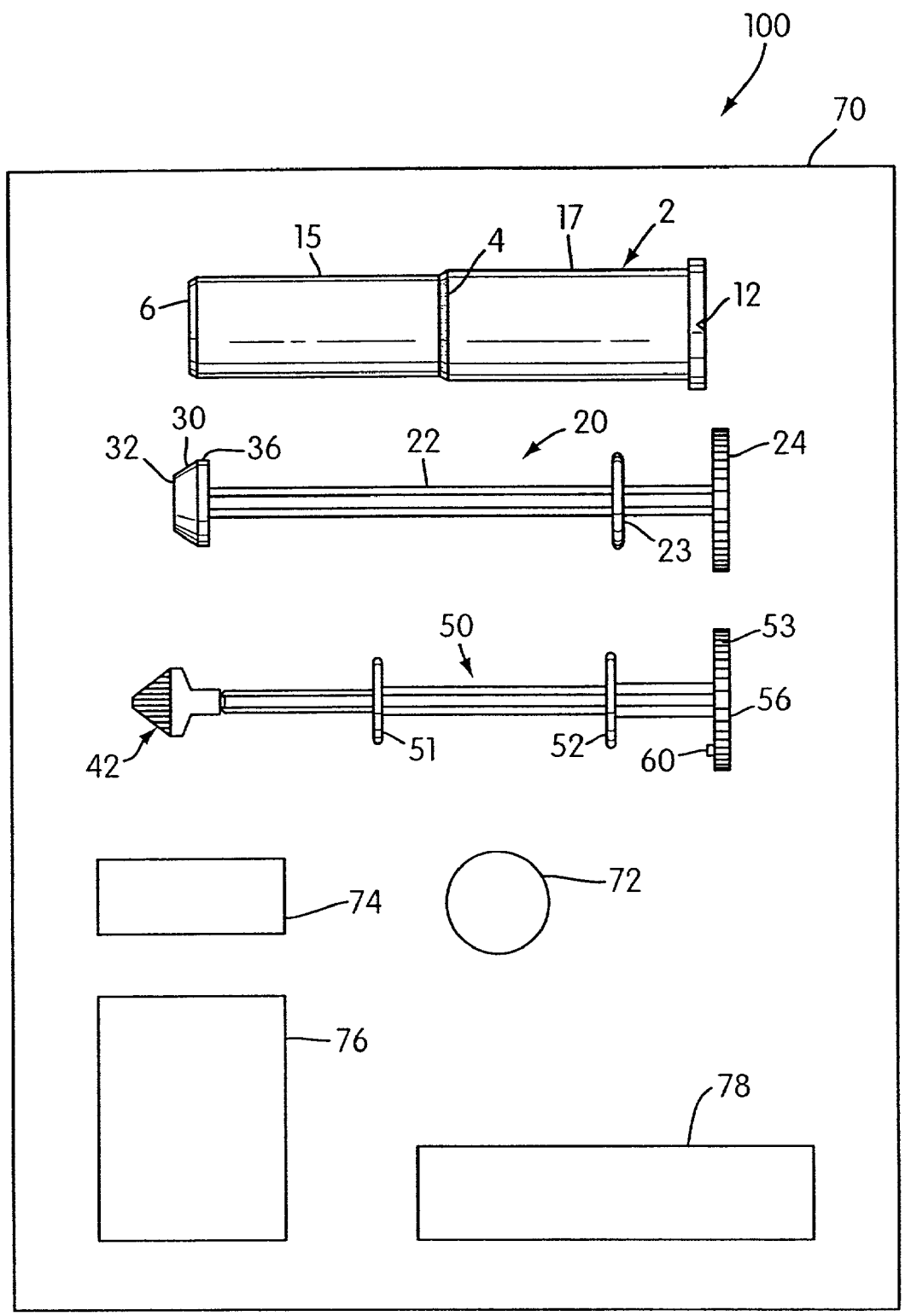
FIG. 1 is a plan view of a portable sampling system for obtaining cervical tissue in accordance to the present invention.

FIG. 1 illustrates a portable cervical tissue sample collecting system 100 for self administered sampling of cervical tissue and vaginal fluids. The sampling system 100 includes a vaginal insertion tube 2, an introduction guide member 20, a cervical sampler 50 including a sample collecting member 42, a collection container 72, a package of a cytofixative 73, a package of surgical lubricant 74, a pair of gloves 76, instructions for collecting samples, and transportation packaging materials 78 for the collected sample. The components discussed above are packaged in the sample collecting system 100 within a single container 70 or other suitable enclosure. In this manner, the sample collecting system 100 will be easily handled by retailers, consumers, and public heath organizations and can be individually mailed to patients who are unable or unwilling to visit a doctor. The enclosure 70 will also maintain the sterility of the various components of the portable sampling system.

Referring to FIGS. 1–8, an overview of a manner of operating the sample collecting system 100 in accordance with the present invention follows. A pre-insertion assembly 10 is formed by placing the introduction guide member 20 within the vaginal insertion tube 2. The assembly 10 is then inserted into a patient after she assumes a predetermined desired position. Once the insertion tube 2 has been inserted to an appropriate depth, such as the midpoint of the total insertion distance, the introduction guide member 20 is removed from the vaginal insertion tube 2. The advancing of tube 2 is continued until it is positioned within the vaginal cavity at a sampling position where the front end 6 of the vaginal insertion tube 2 is located immediately in front of the cervix. The cervical sampler 50 is then inserted into the vaginal insertion tube 2. The sample collecting member 42 is then pushed into contact with cervical tissue, and a cervical tissue sample is collected by rotating the cervical sampler 50. The cervical sampler 50 is then removed from the vaginal cavity and the cervical tissue sample is transferred from the sample collecting member 42 to the collection container 72 that retains a preservative solution. In an alternative embodiment, the sample collecting member 42 is placed in or over the collection container 72 and a cytofixative is poured, dripped or painted onto the collecting member 42 in order to preserve the cells prior to their being shipped to a lab, as discussed below. The collection container 72 is then packaged and sent to a predetermined laboratory for analysis. The laboratory results are then communicated back to the patient or her doctor for review.

Figure 2:
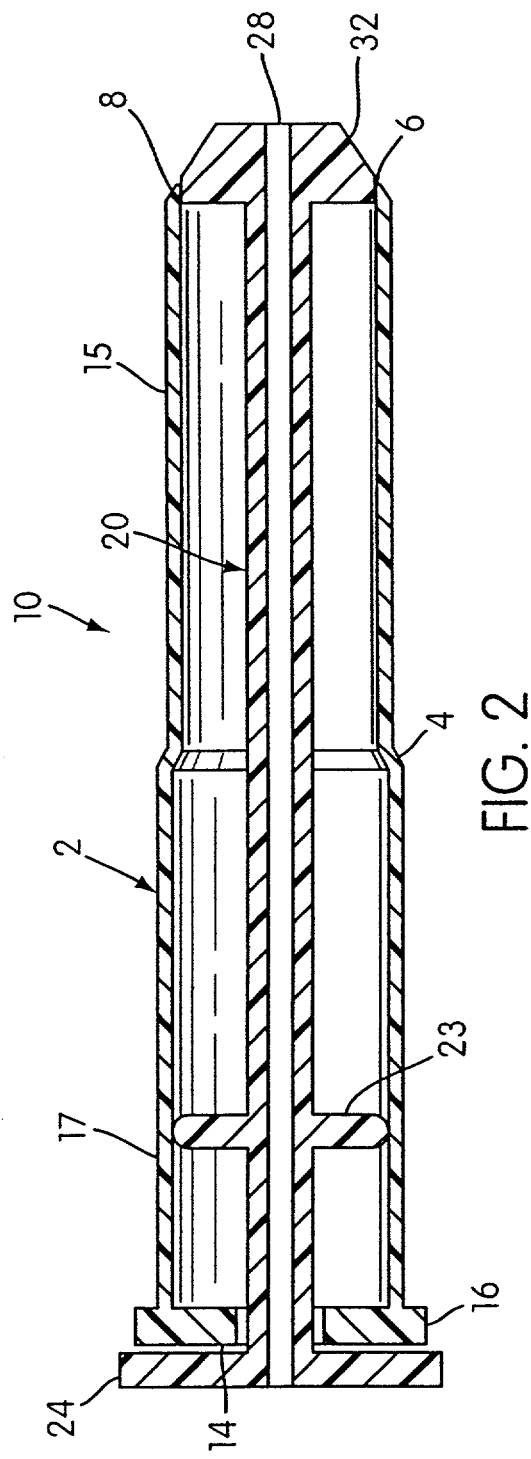
FIG. 2 is a cross-sectional view of a tubular speculum and an introduction guide member in accordance with the present invention.
Figure 3:
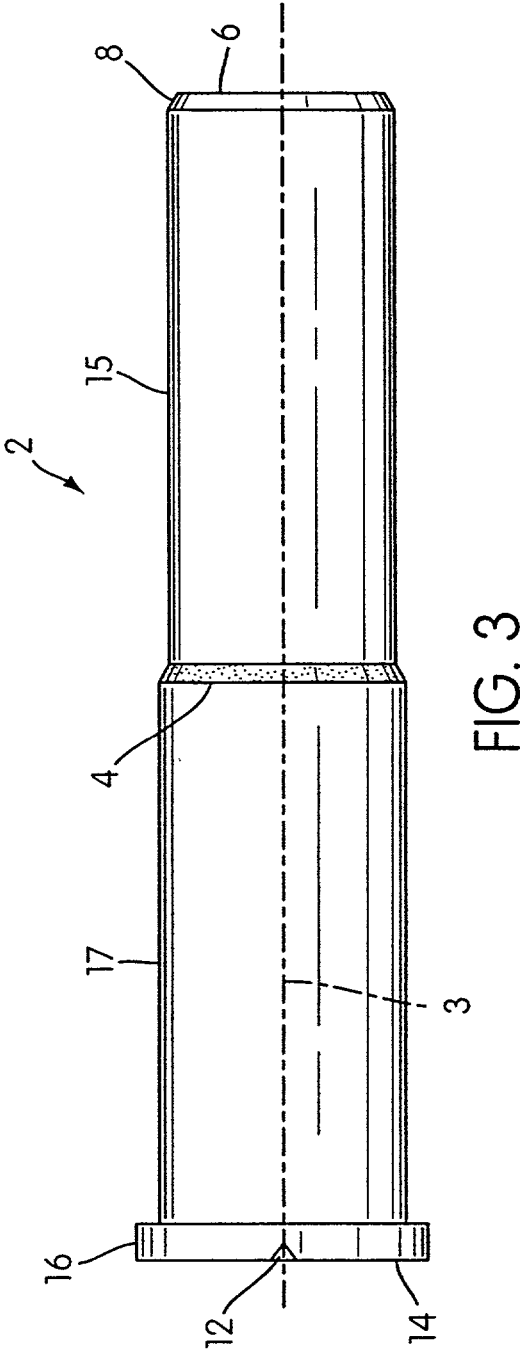
FIG. 3 is a side view of the tubular speculum constructed in accordance with the teachings of the present invention.

Referring to the drawings, there is illustrated in FIG. 2, the vaginal insertion tube 2 and the introduction guide member 20 in a pre-insertion assembly 10. FIG. 3 illustrates the vaginal insertion tube 2, such as a tubular speculum, for opening the vaginal cavity of a patient and providing a passageway in order to collect a cervical tissue sample. The vaginal insertion tube 2 includes a front end 6, an insertion position indicator 4, a rear end 14, an indicator member 12 and a center axis 3.

In a preferred embodiment, the vaginal insertion tube 2 includes a forward cylinder section 15 and a rear cylinder section 17 of which both are integrally formed to provide a single tube. The forward cylinder section 15 includes the front end 6 having a tapered edge 8 that extends outward and rearward from an inner surface of the leading edge of the tube 2. The forward cylinder section 15 has an inner and outer diameter smaller than the rear cylinder section 17. This variance in diameters provides for an advantageous structure to perform the cervical sampling. The rear cylinder section 17 includes the rear end 14 of the vaginal insertion tube 2 having a flange 16, and the indicator member 12, such as a rotator cuff groove or notch portion. The indicator member 12 operates in conjunction with a small protuberance portion 60, such as a rotator cuff, on the handle 56 of the cervical sampler 50 as discussed below. The indicator member 12 and protuberance portion 60 provide an audible and tactile indication each time the user rotates the cervical sampler 50 through a complete revolution and past a reference point. Alternatively, the tube 2 can be one cylindrical section having constant outer and inner diameters throughout its length.

In addition, the tube 2 includes an insertion position indicator 4 having a tactile portion around its outer circumference. The insertion position indicator 4 allows the patient to easily and reliably determine the appropriate depth to insert the vaginal insertion tube 2. The insertion position indicator 4 may also include a surface depression, a step between the forward cylinder section and the rear cylinder section, or a variance in surface texture on the surface of the tube. In a preferred embodiment, the insertion position indicator 4 is located at one-half the length of the tube 2 to indicate the midpoint of the insertion depth. This feature advantageously allows the patient to better judge the depth of insertion into the vaginal cavity by alerting her when half of the tube 2 has been inserted. In addition, the insertion position indicator 4 provides the user with a predetermined time for removing the introduction guide member 20; when the position indicator 4 is proximate to the vaginal walls, the guide member 20 is removed from the vaginal insertion tube 2 and the tube 2 is advanced until located in a sampling position in front of the cervix. Further the insertion position indicator 4 allows the patient to feel the location of the tube relative to the outer tissue of the vagina.

Figure 4:
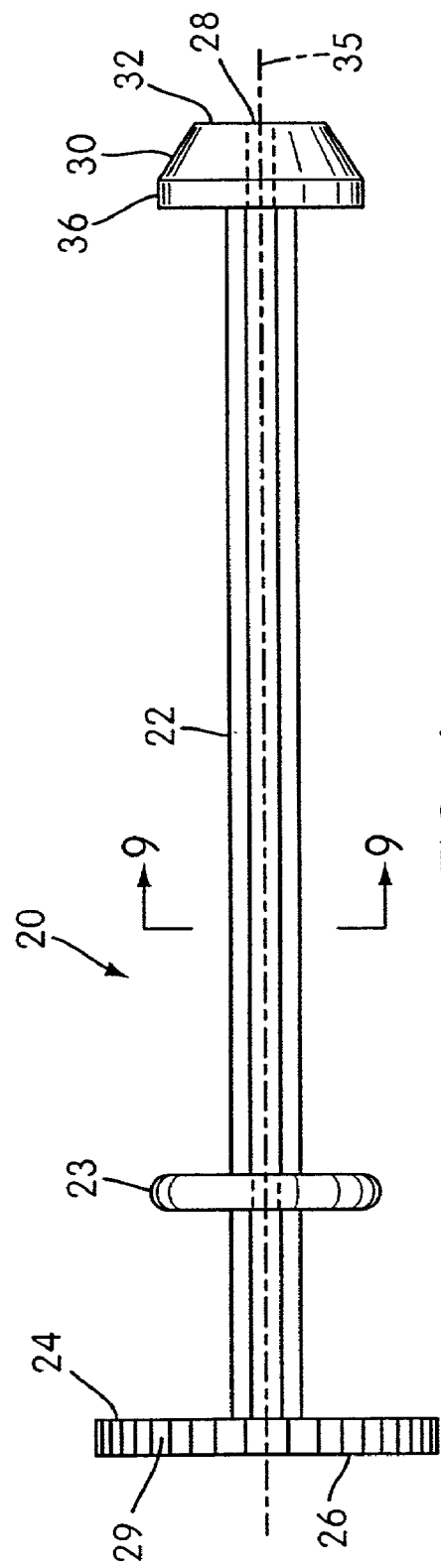
FIG. 4 is a side view of the introduction guide member construction in accordance with the teaching of the present invention.
Figure 9:
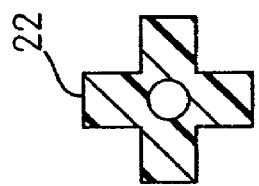
FIG. 9 is a cross section of the elongated member as taken along the lines 9—9 in FIG. 4.

The introduction guide member 20, that assists in distending the vaginal cavity, is illustrated in FIGS. 2 and 4. The introduction guide member 20 preferably includes a guide head 32, an elongated member 22, a support member 23, and a handle 24 at a rear end 26. The guide head 32 includes a tapered-edge nose cone portion 30 integrally formed with a cylinder portion 36. A first leading edge of the nose cone portion 30 is preferably flat so that the user will not be injured by a sharp or pointed edge during insertion. The nose cone portion 30 includes a taper which is generally aligned with tapered edge 8 of tube 2 to create a sufficiently smooth transition between these elements and provide for comfortable and easy insertion of the introduction guide member 20 into the vaginal cavity. The taper of the tapered edge 8 and guide head 32 may range from 25 to 45 degrees relative to the outer surface of the tube 2. In a preferred embodiment, the tapered edge 8 and guide head 32 is approximately 30 degrees. The nose cone portion 30 and cylinder portion 36 are preferably one solid piece formed of plastic material. The guide head 32 preferably has a diameter slightly smaller than the interior diameter of the vaginal insertion tube 2 to allow the introduction guide member 20 to slide, and rotate, if desired, within the vaginal insertion tube 2. A penetrating tubular opening 28 extends through the nose cone portion 30 and the cylinder portion 36 to create a passageway for fluids to pass through the guide head 32 during insertion. The elongated member 22 extends between the guide head 32 and the handle 24 and is aligned with the guide head 32 along the center axis 35 of the introduction guide member 20. As shown in FIGS. 8 and 9, the elongated member 22 preferably has a "X" or cross shaped section but, may be other shapes or cross-sections, such as a square, rectangle, or circle. A passageway may be formed in the elongated member 22 and aligned with the tubular opening 28 to allow fluids to pass through the guide head 32 and out of the assembly 10. This feature allows for easier insertion of the vaginal insertion tube 2 by reducing pressure in the vaginal cavity as a result of providing an open passageway from the forward face of the guide head 32 to the trailing face of the rear end 26 which permits fluid to exit the vaginal cavity through the introduction guide member 20. In a preferred embodiment, the introduction guide member 20 includes at least one support member 23 integrally formed with the elongated member 22. The support member 23 assists in providing lateral stability to the introduction guide member 20 and assists in aligning the guide member 20, when the guide member 20 is inserted into the vaginal insertion tube 2. Alternatively, the support member 23 may be eliminated and the cylinder portion 36 of the guide head 32 may be extended towards the rear end 26. The length of the cylinder portion 36 would be sufficient to provide stability and alignment of the introduction guide member 20 within the tube 2. The length of the cylinder portion may be between 1 to 1.50 inches.

The rear end 26 of the introduction guide member 20 preferably includes a handle 24 that allows the patient or user to insert and remove the introduction guide member 20 from the vaginal insertion tube 2. In a preferred embodiment, the handle 24 is in the shape of a disk having a forward face of the disk integrally connected to the elongated member 22, and a diameter larger than the diameter of the flange 16 of the vaginal insertion tube 2. If desired, the handle 24 may be in any shape such as a rectangle or a cylinder. The handle 24 preferably includes of a tactile portion 29 such as, a straight knurling pattern on the outer edge around the circumference of the disk. This feature provides an advantageous surface to assist the user in grasping and operating the introduction guide member 20. The handle 24 also preferably serves a dual function as a stopping member for the introduction guide member 20. The handle 24 stops motion in the axial direction when the patient fully inserts the introduction guide member 20 into the vaginal insertion tube 2. By the handle 24 stopping the motion of the guide member 20 when in its extended position, the guide head 32 of the introduction guide member 20 preferably has the nose cone portion 30 extending axially away from the front end 6 and substantially aligned with the tapered edge 8 of the vaginal insertion tube 2 for creating a substantially continuous taper that provides for comfortable insertion of the tube 2.

The vaginal insertion tube 2 is preferably constructed from a transparent plastic material, such as a high impact polystyrene (HIPS) crystal. The introduction guide member 20 is constructed preferably from a filled plastic material such as, polypropylene with a calcium carbonate mineral filler. Transparent plastic materials assist the patient in understanding how the vaginal insertion tube 2, introduction guide member 20, and cervical sampler 50 operate, which is an important consideration since the system 100 may be used by a woman with little or no medical training. The plastic material for the vaginal insertion tube 2 and introduction guide member 20 should be preferably lightweight, biocompatible, inert, capable of being sterilized and have a generally smooth surface so they will not injure the user. The plastic material should also be relatively inexpensive so that the production costs are kept low and the system 100 remains affordable. The vaginal insertion tube 2 is preferably 6.5 inches (16 centimeters) in length. The tube 2 is generally cylindrical with the first cylinder section 15 having an outer diameter of approximately 1.25 inches (3.1 centimeters) in order to fit comfortably in the vaginal cavity. Also, the introduction guide member 20 is preferably an approximate 6.81 inches (19.8 centimeters) in length. Other dimensions, however, may be used.

The vaginal insertion tube 2 and the introduction guide member 20 is preferably manufactured or formed in a process such as, injection molding. The components of the introduction guide member 20, e.g., the elongated member 22, support member 23, handle 24, and guide head 32 with integral nose portion 30 and cylinder portion 36, should be formed with a similar process. In a preferred embodiment, insertion position indicator 4 is formed from a step or a transition between the forward 15 and rear 17 cylinder sections. The insertion position indicator 4 on the vaginal insertion tube 2 is formed by a process such as scoring, routing or sanding the outer surface of the tube 2. The processes create a groove, a series or pattern of grooves, surface texture variance, or other types of marks on vaginal insertion tube 2 that a patient can feel with their hands during the insertion of the vaginal insertion tube 2.

Figure 5:
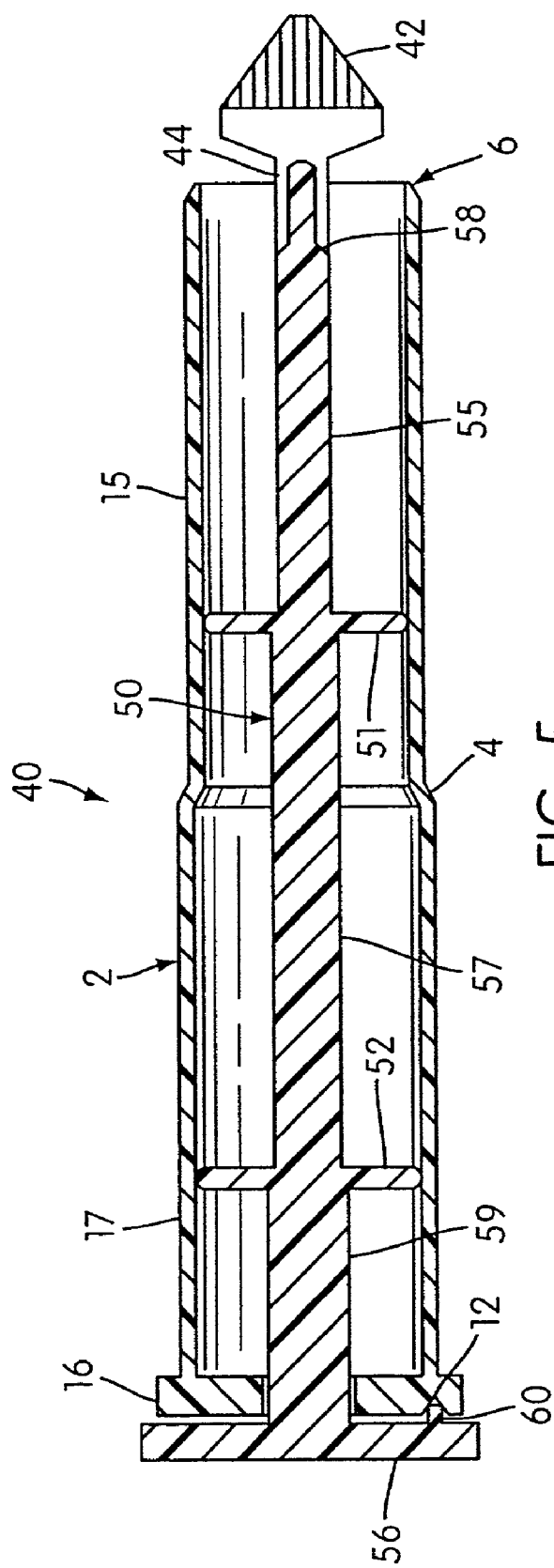
FIG. 5 is a cross-sectional side view of the tubular speculum, and a cervical sampler that includes a sample collecting member according to the prevent invention.

FIGS. 5 illustrates the cervical sampler 50 and the vaginal insertion tube 2 in an assembled position 40. The cervical sampler 50 constructed in accordance with the present invention is illustrated in FIGS. 5–8. The cervical sampler 50 includes a sample collecting member 42 that comes into contact with tissue of the cervix. The sample collecting member 42 removes cervical tissue cells that will be analyzed after the sample collection has been completed. Referring to FIG. 5, the sample collecting member 42, in a preferred embodiment, includes a cervical brush used in gynecological medicine that samples a transformation zone of a cervix, such as the endocervix and ectocervix. The brush is preferably flexible and designed with many extensions or bristles to collect cervical cells. Brushes which can be used are similar to those manufactured by Wallach Surgical Devices and described in U.S. Pat. No. 5,787,891. The sample collecting member 42, however, may include any type of brush, probe, sponge or the like which can similarly be used in gynecological cytology to collect a cervical cell specimen. In a preferred embodiment, the sampling collection member 42 is utilized for an automated or computer assisted Pap test cytological analysis. The sample collecting member 42 should be preferably smaller in width than the inner diameter of the vaginal insertion tube 2 to allow the cervical brush to fit inside of the tube 2.

The cervical sampler 50 includes a holding end 58, alignment members 51, 52, an elongated body in three sections, 55, 57, 59, and an integral disk handle 56. The forward 51 and rear 52 alignment members are used to guide and to align the cervical sampler 50 along the center longitudinal axis 3 of the vaginal insertion tube 2. As shown in FIGS. 5–6, the alignment members 51, 52 move relative to the insertion tube 2, rather than being fixed to the tube 2. As best shown in FIG. 5, the alignment members 51, 52 are integrally formed with and connected to the elongated body as a single unit. The alignment members 51, 52 are also positioned perpendicular to the longitudinal axis 61, such that the alignment members 51, 52 move in conjunction with the elongated body whenever the body slides or rotates within the vaginal insertion tube 2. Also, the alignment members 51, 52 are preferably formed in the shape of a disk and may have different diameters. The diameter of the forward alignment member 51 is preferably small than the diameter of the rear alignment member 52, in order to contact the corresponding diameter of the vaginal insertion tube 2. In a preferred embodiment, the elongated body is in the shape of an "X" or a cross structure. The thickness of the elongated body varies in a forward 55, a middle 57, and a rear 59 section. The forward section 55 extending between the holding end 58 and the forward alignment member 51 is a constant thickness. The middle section 57 extending between the forward alignment member 51 and the rear alignment member 52 has a constant thickness larger than the thickness of the forward section 55. Similarly, the rear section 59 extending between the handle 56 and the rear alignment member 52 has a constant thickness larger than that of the middle section 57. This variance of thickness of the elongated body preferably provides for better resistance to twisting deformation at the rear section 59 and an improved structure when the protuberance portion 60 on the handle 56 contacts the indicator member 12. If desired, other shapes of the elongated body may be utilized, such as a rectangle or cylinder. In addition, the elongated body may be formed as a single constant thickness rod extending between the holding end 58 and the handle 56.

The holding end 58 of the cervical sampler 50 includes a holder 62 that extends axially outward from the holding end 58, and mates with a complimentarily formed internal cavity 44 of the sample collecting member 42. Referring to FIGS. 7–8, the holder 62 includes an elongated protuberance, with a generally symmetrical "X" shape cross section that is integrally formed with the forward section 55 of elongated body and extends there from. This holder 62 supports the sampling collecting member 42, while eliminating additional parts used in previous devices. The "X" or cross shape of the holder 62 includes a plurality of arms 63. In a preferred embodiment, the plurality of arms 63 includes a plurality of hemispherical protuberances 65 that engage corresponding surfaces within the internal cavity 44 of the sample collecting member 42. This engagement improves the transfer of rotational motion of the disk handle 56 to the sample collecting member 42. The mating of the holder 62 and the sample collecting member 42 also creates a frictional contact between the surfaces of complimentary internal cavity 44 of the sample collecting member 42 and the cross structure. The plurality of hemispherical protuberances 65 advantageously increases this frictional contact. The "X" or cross structure also allows the sample collecting member 42 to slide in conjunction with the corresponding movement of the elongated body. In a preferred embodiment, the sample collecting member 42 is removable from the holder 62 at the holding end 58.

Referring FIG. 6, at the rear end of the cervical sampler 50, the disk handle 56 is integrally connected to the rear section 59 of the elongated body at the center of the disk handle 56. In a preferred embodiment, the disk handle 56 extends radially and perpendicularly from the longitudinal axis 61, and includes a tactile portion 53, such as a straight knurling pattern. The disk handle 56 performs several functions. First, the disk handle 56 can be grasped by the patient in order to insert and remove the cervical sampler 50 from the vaginal insertion tube 2. In this manner, the disk handle 56 controls how far the sample collecting member 42 will extend from vaginal insertion tube 2. Second, the disk handle 56 is of sufficient size to allow the patient to grasp the handle 56 and freely rotate the cervical sampler 50 within the vaginal insertion tube 2 and correspondently rotate the sample collecting member 42 extending outside the tube 2, in order to collect the necessary cervical cell sample. In a preferred embodiment, the handle 56 has a diameter larger than that of the vaginal insertion tube 2. Third, in a preferred embodiment, the handle 56 includes the protuberance portion 60, such as a rotator cuff, having a forward extending protuberance that cooperates with the indicator member 12 to create an audible or tactile indication of the completion of a revolution when the user rotates the protuberance past a reference point such as the indicator member 12 during the sampling procedure. The protuberance portion 60 extends from the forward face of the handle 56 in the direction of the sample collecting member 42. The protuberance portion 60 substantially contacts the indicator member 12, such that the audible or tactile indication is produced and communicated to the user.

Referring to FIG. 6, the forward 55, middle 57, and rear 59 sections of the elongated body, the alignment members 51, 52 and the handle 56 are preferably constructed from a plastic material, such as polypropylene having a calcium carbonate filler. Injection molding is a preferred manufacturing process used to form the above mentioned components. The plastic material should be preferably lightweight, relatively inexpensive, capable of being sterilized, biocompatible, inert and have a generally smooth surface.

The cervical sampling apparatus in accordance with the present invention may be used in the following manner. The patient or user fully inserts the introduction guide member 20 into the vaginal insertion tube 2 to form the pre-insertion assembly 10 shown in FIG. 2. The patient substantially aligns the guide head 32 with the tapered edge 8 to allow the nose cone portion 30 to extend outward from the edge 8. Also the patient applies a portion of sterile surgical lubricant 74 to the guide head 32 of the introduction guide member 20 and if desired, the tapered edge 8 of the vaginal insertion tube 2. The patient performs a maneuver, on a substantially horizontal surface, by lying down on her back with her knees bent upward (a modified sit-up position) in which the pelvic floor of the patient is depressed. This maneuver advantageously allows the cervix to align with the tube 2 due to the added effect of creating abdominal pressure during the insertion of the introduction guide member 20 and vaginal insertion tube 2, coupled with the depression of the pelvic floor.

Next, the patient slowly inserts the introduction guide member 20 and vaginal insertion tube 2 into the vagina in order to distend the vaginal cavity and align the axis of the tube 2 with the cervix of the patient. The introduction guide member 20 and vaginal insertion tube 2 are advanced together until the insertion depth indicator 4 is proximate the vaginal walls. When the midpoint depth is reached, the introduction guide member 20 is withdrawn from the vaginal insertion tube 2 which helps reduce the potential for guide member 20 to contact and injure the cervix. During the removal of the guide member 20, the patient retains the position of the tube 2 in the vaginal cavity. After the introduction guide member 20 is removed, the patient further advances the tube 2 into the vaginal cavity until the tube 2 is in a sampling position at the cervix and resistance is felt by the patient. Referring to FIG. 5, the position of the vaginal insertion tube 2 is maintained and the patient inserts the cervical sampler 50 into the tube 2. As discussed above, the alignment members 51, 52 align the center of the sample collecting member 42 with the center axis 3 of the vaginal insertion tube 2 and the cervix.

The patient then applies pressure to the cervical sampler 50 thereby contacting a portion of the cervix with the sample collecting member 42. Next, the patient maintains the position of the vaginal insertion tube 2 and rotates the handle 56 between 5 and 15 complete revolutions—as indicated by the indicator member 12, such as a groove portion, and protuberance portion 60. Depending on brush designs more or less rotations could be employed. In a preferred embodiment, the handle 56 is rotated through ten (10) complete revolutions. In turn, the sample collecting member 42 will also be rotated ten revolutions so as to collect cervical samples. The indicator member 12 and protuberance portion 60 reliably permit the patient to determine when a rotation has been completed. This feature is advantageous to determining the amount of cervical sample collected. In a preferred embodiment, when the indicator member 12 contacts protuberance portion 60, an audible signal is produced which signals the patient that a revolution of the cervical sampler 50 has been completed. Likewise, if a patient has difficulty in determining the audible signal, the feature can also provide a tactile signal, such as vibration of the indicator member 12 or contacting a finger of the user as the cervical sampler 50 completes each full revolution. The audible and tactile signaling feature is advantageous because the patient is laying on her back, holding the vaginal insertion tube 2 in one hand and with the other hand turning or rotating the cervical sampler 50, therefore, she cannot see or will have difficulty seeing when a complete revolution has been accomplished.

In a preferred embodiment, after the appropriate number of rotations, such as ten, the proper amount of cervical sample has been collected. The patient removes the cervical sampler 50 from the vaginal insertion tube 2, and subsequently withdraws the vaginal insertion tube 2 from the vaginal cavity. In one embodiment, the sample collection portion 42 is then removed from the remainder of the cervical sampler 50 and placed into the collection container 72, such as a vial, that in one embodiment, as discussed above, retains thin layered liquid preservative solution used in gynecological cytology, such as AutoCyte PREP available from Tri Path Imaging. This method advantageously allows for using substantially automated screening of the cervical sample to reduce the diagnosis problems associated with a manual method of screening. Alternatively, the sample collecting member 42 is not released from the holder 62 and placed in the collection container 72. Instead, the sample collecting member 42 remains connected to elongated body forward section 55 and is swirled, agitated, or washed in a methanol based preservative solution, such as those available from Cytyc, to remove the cervical cells. In general, the above preservative solutions provide for preservation of cervical cells for future analysis in gynecological cytology. Once the sample is collected, the collection container 72 is sealed, labeled and transported to a predetermined laboratory for analysis. In this embodiment, the laboratory includes automated or computer assisted diagnosis equipment for analysis of the cervical sample collected by the patient. After the cells have been transferred to the solution or analyzed, the sample collecting member 42 may discarded. Once the laboratory completes the analysis of the cervical sample, the results are communicated back to the patient. The diagnosis tests procedures do not form any part of this invention.

As is known in the art, these types of specially formulated preservative solutions need to be supplied in the sample collection container 72 or else the collected cytology sample will not be properly and effectively preserved so that the lab can prepare useful slides. Conventional ethanol alcohol based fixatives used to prepare slides are not effective for preserving a sample when provided to a patient in the sample collection container 72. As a result, the specially formulated preservative solutions were provided with the system and provided to the patient. These specially formulated preservative solutions are significantly more expensive than conventional, ethanol based fixatives.

Figure 10:
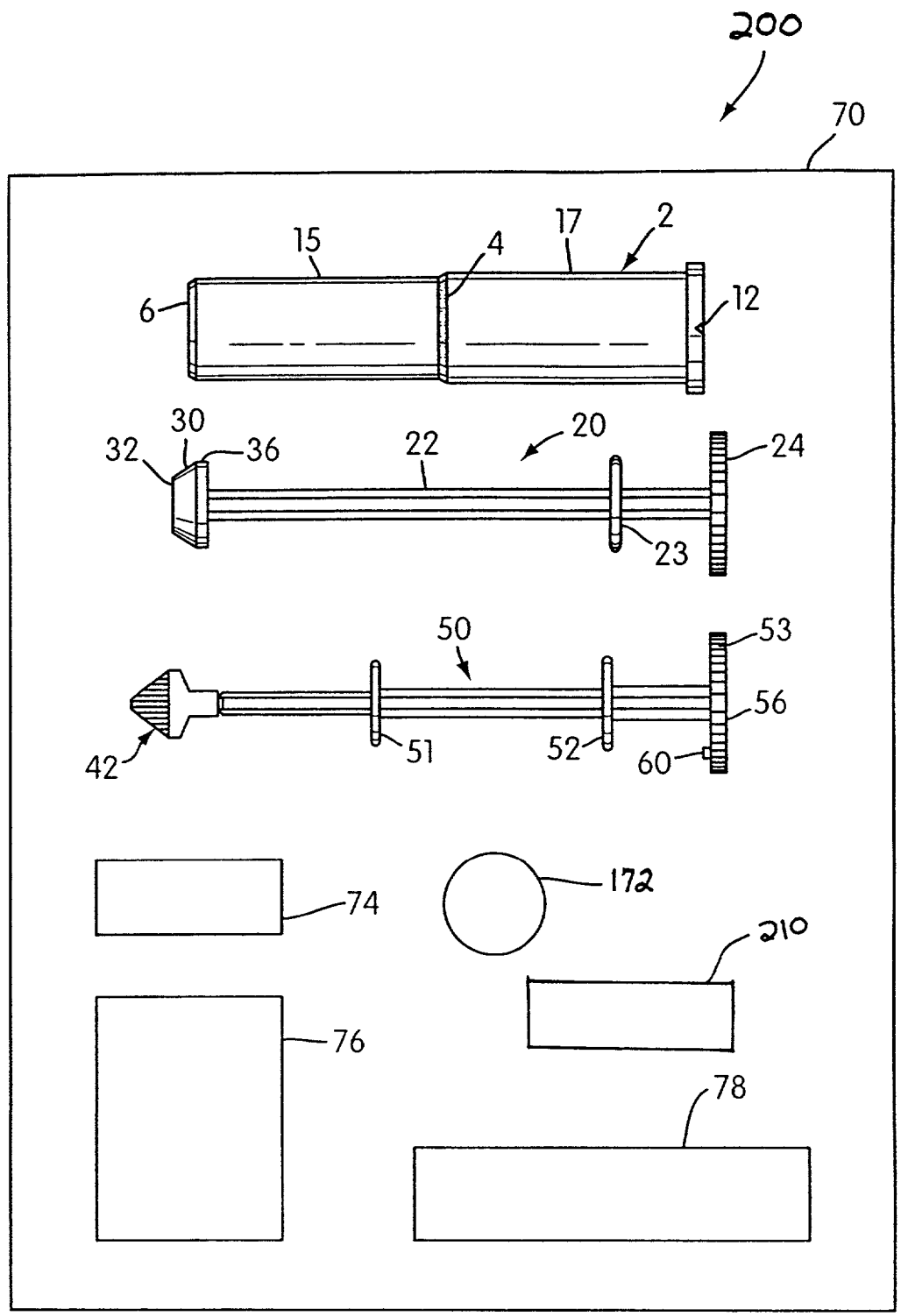
FIG. 10 is a plan view of a portable sampling system for obtaining cervical tissue in accordance to the present invention including a cytofixative stored in a container that is separate from the sample collection container.

In another embodiment, sample collecting system 200 illustrated in FIG. 10 is the same as system 100, except it differs in the following manner. The sample collecting system 100 does not include a sample collection container 72 carrying a preservative solution like that discussed above with respect to system 100. Sample collection container 172 does not carry a fixative solution; it is intended to be delivered empty to the patient or the health care professional. The system 200 also includes a container 210 of a conventional cytofixative used to prepare sample slides. The container 210 can be a tube, package, packet or any other type of fluid carrying container. One such conventional fixative is an ethanol alcohol based fixative such as "Safetex" available from Adwin Scientific of Canoga Park, Calif. This fixative is at least 95% ethanol alcohol and 2.5% carbowax. It can also be 97.5% ethyl alcohol and 2.5% carbowax. The remainder of the system 200 is the same as system 100.

In preserving the sample collected with sample collecting member 42 provided with system 200, the method of using system 200 differs somewhat from that of system 100. After the sample has been collected, using sample collecting member 42, the sample collecting member 42 is positioned in or over the empty sample collection container 172. The container 210 of the fixative is opened. The fixative is then "applied onto" the sample collecting member 42. "Applied onto" as used herein is meant to describe the situation where the fixative is poured, dropped, dripped, sprayed or otherwise placed onto the sample collecting member 42 without submerging or delivering the member 42 into any amount of collected fixative solution. As mentioned above, the placing of the sample collecting member 42 into an amount of a conventional fixative, such as Safetex, will not be properly preserve the sample for later slide preparation at a lab. Instead, it will be clumped, contain many body fluids and make it very difficult, if not impossible, for a lab technician to make readable slides. While it is unclear why applying the fixative onto the sample collecting member 42 properly and effectively preserves the collected cells as well or better than the specially formulated preservative solutions discussed in system 100, it is unknown why the cells are not properly preserved when the sample collecting device 42 is placed into a container, such as container 72, carrying the conventional fixative.

The amount of conventional fixative applied onto the sample collecting member 42 from container 210 can vary depending on the size of the sample. For example, about 20 to 50 drops of the cytofixative from container 210 can be applied onto the sample collecting member 42. In another embodiment, between about 25 and 40 drops are applied. In another embodiment about 30 drops are applied onto the sample collecting member 42. The number of drops or total amount sprayed or otherwise applied onto the member 42 would equal about between 0.5 and 20 ml. The amount of the fixative from container 210 will depend, at least in part, on the size of the sample.

While these particular embodiments of the invention has been shown and described, it is recognized the various modifications thereof will occur to those skilled in the art. Therefore, the scope of the herein-described invention shall be limited solely by the claims appended hereto.

What is claimed is:

1. A cervical sampling apparatus, comprising:
   a vaginal insertion tube;
   an introduction guide member for being removably positioned within the vaginal insertion tube, the introduction guide member extending beyond an end of the tube when inserted therein for guiding the vaginal insertion tube into a vaginal cavity;
   a cervical sampler for being slidably and rotatably disposed in the vaginal insertion tube after the introduction guide member is removed from the vaginal insertion tube, the cervical sampler comprising a sample collecting member for obtaining a cervical sample when positioned within the vaginal cavity, a forward end including a holder for mating with the sample collecting member and a rear end for grasping by an operator; and
   an insertion position indicator located along a length of the vaginal insertion tube, wherein the insertion position indicator includes a discontinuity along the vaginal insertion tube that can be felt by a user.

2. The apparatus of claim 1, wherein the rear end of the cervical sampler includes a handle.

3. The apparatus of claim 2, wherein the holder mates with the sampling collecting member such that the sample collecting member rotates when the handle is rotated.

4. The apparatus of claim 2, wherein the cervical sampler further includes at least two alignment members that align the cervical sampler with a longitudinal axis of the vaginal insertion tube when the cervical sampler is positioned within the vaginal insertion tube.

5. The apparatus of claim 4, wherein the alignment members are integrally formed with an elongated portion of the cervical sampler.

6. The apparatus of claim 2, wherein the vaginal insertion tube includes a signaling member for cooperating with a signaling member of the cervical sampler to indicate to the user when the handle has been rotated past a reference point.

7. The apparatus of claim 6, wherein the signaling member of the cervical sampler includes a protuberance.

8. The apparatus of claim 6, wherein the signaling member of the vaginal insertion tube includes a notch.

9. The apparatus of claim 1, wherein the introduction guide member includes a forward end and a rear end, the forward end of the introduction guide member having a guide head including a tapered portion, the rear end of the introduction guide member having a stop member.

10. The apparatus of claim 9, wherein the tapered portion of the guide head is substantially aligned with a tapered edge of the vaginal insertion tube for creating a substantially continuous tapered surface.

11. The apparatus of claim 9, wherein the guide head of the introduction guide member includes an elongated inner passageway for allowing fluid from the vaginal cavity to enter the guide head.

12. The apparatus of claim 11, wherein the introduction guide member further includes an elongated member extending between the guide head and the rear end, the elongated member having an internal passageway aligned with the passageway in the guide head for allowing fluid to exit the vaginal cavity through the introduction guide member.

13. The apparatus of claim 1, wherein the sample collecting member includes a cervical sample brush.

14. A method for cervical sampling, said method comprising the steps of:
   introducing a cervical sampling member into a vaginal cavity;
   collecting a cervical sample from the vaginal cavity using the cervical sampling member;
   removing the cervical sampling member from the vaginal cavity; and
   applying an ethanol based fixative onto the cervical sampling member carrying the cervical sample;
   wherein the step of introducing the cervical sampling member into the vaginal cavity includes the steps of:
   a) inserting an introduction guide member into a vaginal insertion tube so that a portion of the introduction guide member extends outwardly from a forward end of the vaginal insertion tube;
   b) introducing and advancing the vaginal insertion tube along with the inserted introduction guide member into the vaginal cavity;
   c) withdrawing the introduction guide member from the vaginal insertion tube;

d) advancing the vaginal insertion tube further into the vaginal cavity after withdrawing the introduction guide member until the vaginal insertion tube has reached a sampling position;

e) inserting the cervical sampling member including a sample collecting member into the vaginal insertion tube; and f) extending the sample collecting member into the vaginal cavity from an end of the vaginal insertion tube.

15. The method of claim 14 wherein the step of collecting a cervical sample comprises the step of contacting a portion of cervical tissue within the vaginal cavity with the sample collecting member.

16. The method of claim 14, further comprising the step of coating the introduction guide member with a surgical lubricant.

17. The method of claim 15, further comprising the steps of removing the sample collecting member from a holder portion of a cervical sampler after the fixative has been applied onto the sample collecting member.

18. The method of claim 14, wherein the step of inserting the cervical sampling member includes substantially maintaining the vaginal insertion tube within the vaginal cavity at a sampling position.

19. The method of claim 14, wherein the step of withdrawing the introduction guide member from the vaginal insertion tube further includes substantially maintaining the position of the vaginal insertion tube as the introduction guide member is withdrawn.

20. The method of claim 14, wherein the step of advancing the vaginal insertion tube and the inserted introduction guide member into the vaginal cavity includes the step of advancing the vaginal insertion tube until a mid-point of the vaginal insertion tube is substantially proximate a wall of the vaginal cavity.

21. The method of claim 14, wherein the step of collecting a cervical sample with the sample collecting member includes rotating the cervical sampling member at least ten complete revolutions.

22. The method of claim 14 wherein the step of applying the ethanol based fixative onto the cervical sampling member includes the step of dripping, pouring or spraying the fixative onto the cervical sample.

* * * * *